United States Patent [19]

Meijer

[11] Patent Number: 4,751,476

[45] Date of Patent: Jun. 14, 1988

[54] DETECTOR DEVICE AND METHOD FOR DISTINGUISHING BETWEEN FLUIDS HAVING DIFFERENT DIELECTRIC PROPERTIES

[75] Inventor: Robert Meijer, San Diego, Calif.

[73] Assignee: Fisher Scientific Company, San Diego, Calif.

[21] Appl. No.: 99,314

[22] Filed: Sep. 21, 1987

[51] Int. Cl.⁴ .......................................... G01N 27/00
[52] U.S. Cl. ................................... 331/65; 340/632; 128/DIG. 13
[58] Field of Search .................. 331/65; 340/603, 607, 340/608, 632; 128/DIG. 13; 73/200

[56] References Cited

U.S. PATENT DOCUMENTS

| | | | |
|---|---|---|---|
| 3,553,575 | 1/1971 | Shea | 331/65 X |
| 4,114,144 | 9/1978 | Hyman | 340/632 |
| 4,367,736 | 1/1983 | Gupton | 128/214 E |
| 4,449,122 | 5/1984 | Whitmer | 331/65 X |
| 4,565,500 | 1/1986 | Jeensalute et al. | 417/53 |

Primary Examiner—Eugene R. LaRoche
Assistant Examiner—Robert J. Pascal
Attorney, Agent, or Firm—Workman, Nydegger & Jensen

[57] ABSTRACT

A device and method for distinguishing between different fluids on the basis of their dielectric properties. In an preferred embodiment, the device comprises two substantially parallel conductive surfaces which are positioned on opposite sides of a fluid conduit so as to form a substantially parallel plate capacitor. The first conductive surface is electrically connected through an inductor to a voltage source, and such first conductive surface is also electrically connected to the source electrode of a field-effect transistor. A resonator device is electrically connected between the second conductive surface and the gate electrode of the field-effect transistor. The gate electrode of the field-effect transistor is further electrically connected through a fixed resistance to ground, and the drain electrode of the field-effect transistor is electrically connected directly to ground. The inductance of the inductor is selected such that the resonant frequency of the inductor and the capacitor is substantially the same as the operating frequency of the resonator device when a desired column of fluid is positioned between the two conductive surfaces. In this state, the output voltage of the detector device will oscillate. However, when a column of fluid having significantly different dielectric properties is positioned between the two conductive surfaces, the resonant frequency of the inductor and the capacitor will change, and the output voltage of the detector device will stop oscillating.

23 Claims, 1 Drawing Sheet

DETECTOR DEVICE AND METHOD FOR DISTINGUISHING BETWEEN FLUIDS HAVING DIFFERENT DIELECTRIC PROPERTIES

BACKGROUND

1. The Field of the Invention

This invention relates to devices and methods for distinguishing between different kinds of fluids and, more particularly, to a novel device and method for distinguishing between liquids and gases on the basis of their differing dielectric properties. This invention is particularly, but not exclusively, useful as an air-in-line detector for an IV infusion device.

2. The Background Art

Various kinds of fluid systems are currently in wide use in industrial, medical and many other applications. As used herein, the term "fluid" refers generally to any substance which is not solid and which is capable of flowing through a tube or conduit and, thus, includes both gases and liquids.

In fluid systems, it is often desirable to be able to distinguish between different fluids, such as, for example, water and air. Such detection is essential for the proper operation of many fluid systems.

For example, a fluid system may be intended to convey a liquid through a conduit. If sufficient quantities of air enter the conduit, however, the system may malfunction. For instance, if the system includes a pump for conveying the liquid through the conduit, the pump may cease to operate properly in the presence of sufficient quantities of air. The intended function of the system will, in any event, not be served unless the air is detected and removed from the system.

In fluid systems which are intended for medical applications, the early detection of an air bubble in a column of liquid can be vital. For example, a patient is often supplied with medication or other essential liquids through a tube which is connected to the patient through an intravenous (IV) catheter. If air bubbles enter the tube and are conveyed to the patient, the patient can be subjected to significant discomfort. Such air bubbles can in some cases even become life-threatening.

In order to insure the proper operation of fluid systems, especially those intended for medical use, those skilled in the art have attempted to develop devices that will automatically detect an air bubble in a column of liquid. Unfortunately, however, the prior art devices have typically been somewhat limited in their application, such as, for example, being limited to use with either an opaque liquid or a substantially transparent liquid. Those prior art systems which have been intended for use with both transparent liquids and opaque liquids have generally been quite complex and expensive, and also somewhat unreliable.

One type of system which is commonly used to detect the presence of an air bubble in a column of liquid uses a light source which is directed through the column. A photocell or some other light sensitive device is positioned adjacent the fluid column opposite the light source. Then, by detecting the intensity of the light transmitted through the column, the nature of the fluid in the column is ascertained.

For example, if an opaque liquid is being conducted through a transparent conduit, the absence of light transmitted through the conduit is indicative of liquid being in the column. If an air bubble enters the conduit, however, the fluid column will suddenly become transparent. This can be readily detected with the photocell and communicated to appropriate control circuitry.

When the liquid being conveyed through a transparent conduit is also substantially transparent, however, detecting an air bubble in the conduit becomes somewhat more challenging. In such cases, prior art detection devices are often based upon the different light transmission properties of air and liquid. For instance, liquid will generally cause a light beam to be refracted as it passes through the conduit, while air will not. Thus, if the photocell is carefully positioned and shielded so as to detect only a refracted light beam, the detection of light by the photocell is an indication that clear liquid is in the conduit. On the other hand, when such a properly positioned and shielded photocell does not detect a significant amount of light, it is likely that air or an opaque fluid is in the conduit.

It will be readily appreciated that the above-described devices for detecting the presence of an air bubble in a column of liquid are quite complex. These devices require careful alignment and/or shielding of the light source and the photocells. Additionally, when these detection devices are to be used with both opaque and transparent liquids, some means must be provided for initially detecting whether a given liquid is either opaque or transparent. This again adds complexity and cost to the devices and may tend to make their performance somewhat unpredictable.

In addition to photo-optical systems, various ultrasonic devices have also been proposed for the detection of an air-in-line condition. Ultrasonic devices, unlike the photo-optical devices, are not affected by fluid opacity. Instead, they depend on differences in the ultrasonic transmissive properties of the fluid in the tube to distinguish between whether a liquid or a gas is flowing through the tube. Ultrasonic air-in-line detection devices, like sophisticated photo-electric devices, however, are relatively more expensive to manufacture.

The present invention recognizes that an air-in-line condition can be detected by means that are reliable yet less expensive than the optical or ultrasonic systems. In accordance with the present invention, an air-in-line condition can be detected by effectively incorporating the fluid tube as a component of an electrical circuit. Specifically, the present invention takes advantage of the capacitive changes between an air-in-line condition and a liquid-in-line condition to determine when there is an unwanted air-in-line condition.

BRIEF SUMMARY AND OBJECTS OF THE INVENTION

In view of the foregoing, it is a primary object of the present invention to provide a simple electrical device which can readily distinguish between liquids and gases in a fluid column.

It is also an object of the present invention to provide a device for distinguishing between different fluids whose operation is substantially independent of the optical or acoustic properties of the fluid.

It is a further object of the present invention to provide a device for distinguishing between different fluids which is inexpensive to manufacture and reliable in operation.

Also, it is an object of the present invention to provide a device which can readily be used in medical applications to rapidly detect an air bubble in a column of virtually any liquid.

Consistent with the foregoing objects, the present invention is directed to a novel device and method for distinguishing between different fluids on the basis of their dielectric properties. The device comprises two substantially parallel conductive surfaces which are positioned on opposite sides of a column of fluid so as to form a substantially parallel plate capacitor. The first conductive surface is electrically connected through an inductor to a voltage source. A resonator device is electrically connected to the second conductive surface, and a transconductance amplifier means is electrically connected between the resonator device and the first conductive surface.

The inductance required by the device is ascertained by first determining the capacitance of the two conductive surfaces when a typical desired liquid is in the fluid column. The inductance is then selected such that the resonant frequency of the inductor and the capacitor is substantially the same as the oscillating frequency of the resonator device.

Thus, the output voltage of the detector device will oscillate whenever the fluid column is filled with the desired liquid. However, when a fluid having significantly different dielectric properties passes through the fluid column (such as, for example, air), the effective capacitance of the capacitor will change, thereby changing the resonant frequency of the inductor and the capacitor. Consequently, since the resonant frequency will no longer be substantially the same as the operating frequency of the resonator device, the output voltage of the detector device will stop oscillating. Hence, one can readily distinguish between different fluids in the fluid column.

These and other objects and features of the present invention will become more fully apparent from the following description and appended claims, taken in conjunction with the accompanying drawings.

DETAILED DESCRIPTION OF THE PREFERRED EMBODIMENT

It will be readily appreciated that the components of the present invention, as generally described and illustrated in the figures herein, could be arranged and designed in a wide variety of different configurations. Thus, the following more detailed description of the embodiment of the device and method of the present invention, as represented in FIGS. 1 through 3, is not intended to limit the scope of the invention, as claimed, but it is merely representative of one presently preferred embodiment of the invention.

The presently preferred embodiment of the invention will be best understood by reference to the drawings, wherein like parts are designated with like numerals throughout.

Figure 1:
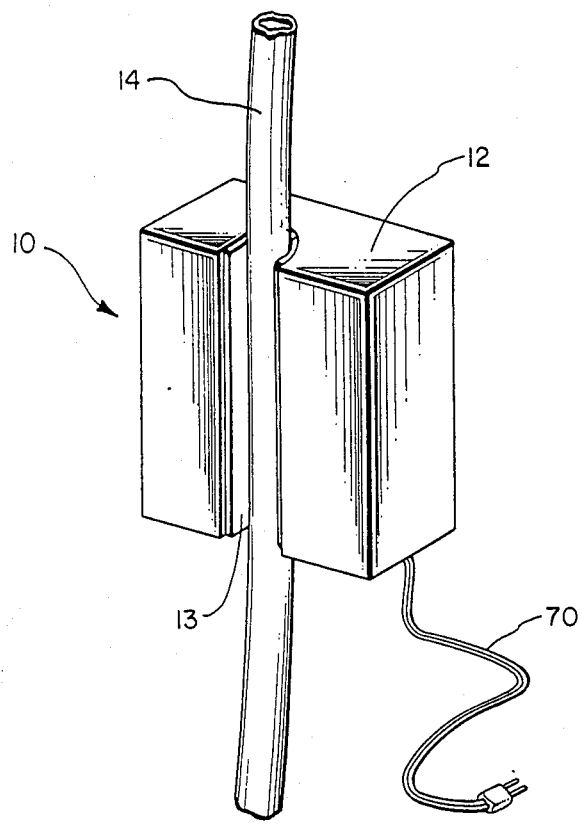
FIG. 1 is a perspective view of the detector device of the present invention showing how the device is used in connection with a substantially non-conductive fluid conduit.

One presently preferred embodiment of the detector device of the present invention, designated generally at 10, is illustrated in its entirety in FIG. 1. As shown, detector device 10 comprises a housing 12 which may be formed of plastic or some other suitable material. Importantly, housing 12 has a channel or groove 13 formed therein for receiving a substantially non-conductive fluid conduit 14.

Figure 2:
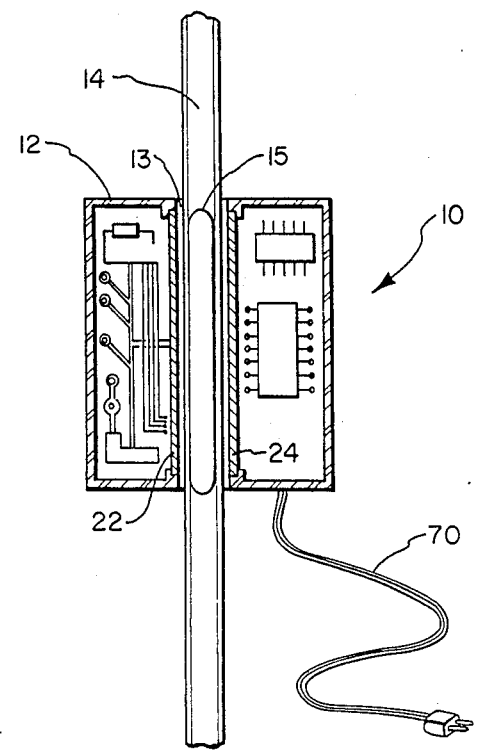
FIG. 2 is a cross-sectional view of the embodiment of FIG. 1 taken along lines 2—2 of FIG. 1 and showing an air bubble in the fluid conduit.
Figure 3:
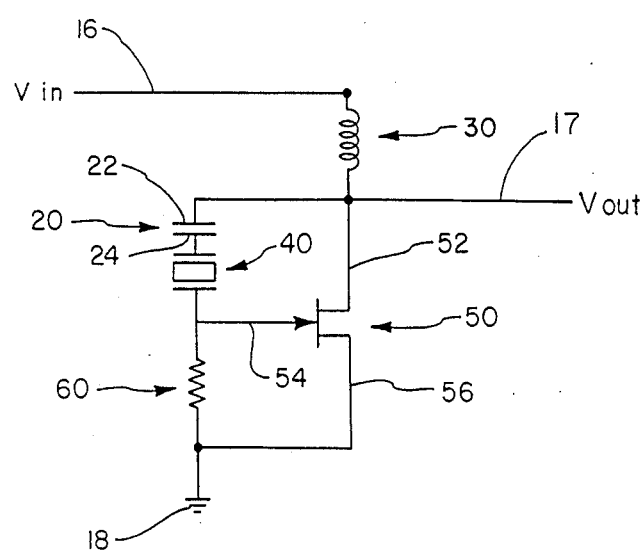
FIG. 3 is one presently preferred embodiment of the electrical circuitry of the detector device of the present invention.

As shown in FIG. 2, two conductive surfaces 22 and 24 are affixed to or embedded within housing 12 in proximity to channel 13. Conductive surfaces 22 and 24 form the plates of a capacitor 20 (see FIG. 3). Importantly, for reasons which will become apparent from the discussion which follows, conductive surfaces 22 and 24 are positioned adjacent channel 13 so as to lie on substantially opposite sides of a conduit 14 which is located within channel 13.

Conductive surfaces 22 and 24 are illustrated in FIG. 2 as being substantially planar, parallel surfaces. However, conductive surfaces 22 and 24 may have virtually any suitable shape and still serve their essential function as a capacitor. Moreover, one advantage of the detector device 10 of the present invention is that conductive surfaces 22 and 24 do not need to be precisely aligned, thus making it easier and less expensive to manufacture detector device 10.

The electrical circuitry of detector device 10 may be conveniently positioned within housing 12, as shown generally in FIG. 2. Such circuitry can then be connected to an appropriate power source and to suitable monitoring devices by means of a cable 70. One presently preferred embodiment of the electrical circuitry of detector device 10 is illustrated schematically in FIG. 3.

As shown in FIG. 3, conductive surface 22 of capacitor 20 is electrically connected to a voltage source 16 through an inductor 30. Conductive surface 22 is also electrically connected to the source electrode 52 of a field-effect transistor (FET) 50.

A resonator device 40 is electrically connected between conductive surface 24 of capacitor 20 and the gate electrode 54 of FET 50. Gate electrode 54 of FET 50 is further electrically connected through a resistor 60 to ground 18, and the drain electrode 56 of FET 50 is connected directly to ground 18.

Resonator 40 comprises an electrical network which is designed to oscillate at a specific frequency. Resonator 40 may, for example, comprise the resonator device which is currently available from Frequency Control Products as part No. FCP 35, and which is designed to oscillate at a frequency of 3.579 Mega Hertz (MHz).

As will be appreciated by those skilled in the art, FET 50 and resistor 60 form a transconductance amplifier in a feedback loop between the output of resonator 40 and the junction between capacitor 20 and inductor 30. The purpose of this transconductance amplifier in detector device 10 is to maintain an operative current level which will allow resonator 40 to oscillate at a substantially constant frequency. A suitable transconductance amplifier circuit could, of course, be configured a number of different ways. The FET amplifier circuit illustrated in FIG. 3 is presently preferred because of its simplicity.

FET 50 is an n-channel FET and can readily be obtained from a number of different sources. For example, one suitable FET 50 is currently available from National Semiconductor as part No. 2N3918.

The purpose of resistor 60 is to adjust the gain of and properly bias FET 50. A suitable resistance value for resistor 60 when using the FET 50 described above is 10 meg Ohms.

It is well known that capacitor 20 and inductor 30 have a resonant frequency at which they will oscillate. Such resonant frequency is directly dependent upon the capacitance of capacitor 20 and the inductance of inductor 30. This relationship can be expressed mathematically, as follows:

$$f = \frac{1}{2\pi \sqrt{LC}} \quad (1)$$

where
f=the resonant frequency (Hz);
L=the inductance of inductor 30 (henries); and
C=the capacitance of capacitor 20 (farads).

Significantly, when the resonant frequency of capacitor 20 and inductor 30 is substantially equal to the oscillating frequency of resonator 40, detector device 10 will produce an oscillating output voltage at 17. On the other hand, if the resonant frequency of capacitor 20 and inductor 30 is significantly different from the oscillating frequency of resonator 40, the output voltage 17 of detector device 10 will be substantially constant. Thus, detector device 10 can be designed to produce an oscillating output voltage 17 under certain desired conditions by properly selecting the inductance of inductor 30 in relation to the capacitance of capacitor 20.

The capacitance of capacitor 20 is dependent upon the surface area of conductive surfaces 22 and 24, the distance between conductive surfaces 22 and 24, and the dielectric properties of the material between conductive surfaces 22 and 24. For example, the capacitance of an ideal parallel plate capacitor is approximated by the following equation:

$$C = \frac{K\epsilon_0 A}{d} \quad (2)$$

where
C=capacitance (farads);
K=dielectric constant of material between capacitor plates;
$\epsilon$=permittivity constant ($8.85 \times 10^{-12}$ farad/meter);
A=surface area of capacitor plates (meter$^2$); and
d=distance between capacitor plates (meters).

Due to fringing and other effects, the actual capacitance of capacitor 20 will be different from the value given by equation (2). Equation (2) does, however, illustrate in a general way how the capacitance of capacitor 20 will depend upon the size and position of conductive surfaces 22 and 24, as well as upon the dielectric nature of the specific material which separates conductive surfaces 22 and 24.

In using detector device 10, the inductance of inductor 30 is selected so that the resonant frequency of capacitor 20 and inductor 30 is substantially the same as the oscillating frequency of resonator 40 when a desired column of fluid is positioned between conductive surfaces 22 and 24 of capacitor 20. This can be done by measuring the capacitance of capacitor 20 with the desired column of fluid in place and then selecting an inductor 30 having a fixed inductance of the required value. Alternatively, inductor 30 may be a variable inductance device which can be adjusted so as to provide the necessary inductance for each desired application.

With the inductance of inductor 30 properly selected, the output voltage 17 of detector device 10 will oscillate as long as the desired column of fluid remains between conductive surfaces 22 and 24. However, in the event the column of fluid between conductive surfaces 22 and 24 is interrupted by a column of fluid having different dielectric properties, the capacitance of capacitor 20 (and consequently the resonant frequency of capacitor 20 and inductor 30) will be changed. In such case, the resonant frequency of capacitor 20 and inductor 30 will no longer be substantially the same as the oscillating frequency of resonator 40, and the output voltage 17 of detector device 10 will cease oscillating.

For example, the dielectric constant "K" of air is approximately 1.00054, while the dielectric constant of water is approximately 78. Thus, in accordance with equations (1) and (2), if a column of water between conductive surfaces 22 and 24 is replaced by a column of air, the capacitance of capacitor 20 will decrease by a factor of approximately 78 and the resonant frequency of capacitor 20 and inductor 30 will increase by a factor of approximately 8.8. Hence, if detector device 10 has been designed to produce an oscillating output voltage 17 when a column of water is positioned between conductive surfaces 22 and 24, the output voltage 17 of detector device 10 will cease to oscillate if the column of water is replaced by a column of air.

Those skilled in the art will recognize that the sensitivity of detector device 10 can be selected by varying the dimensions of conductive surfaces 22 and 24 and the 'Q' of the LC circuit. As a general rule, the space between conductive surfaces 22 and 24 should be approximately just large enough to receive the smallest volume of fluid one desires to detect. For example, the embodiment of detector device 10 illustrated in FIG. 2 could readily detect the presence of air bubble 15, since air bubble 15 occupies virtually the entire space between conductive surfaces 22 and 24. Detector device 10 might not, however, be able to detect air bubbles which are significantly smaller than air bubble 15 because such air bubbles might not be large enough to significantly affect the capacitance of capacitor 20.

Those skilled in the art will also appreciate that conductive surfaces 22 and 24 need not necessarily be in direct contact with the column of fluid. In fact, as shown in FIGS. 1 and 2, the column of fluid will generally reside within some type of conduit. Further, conductive surfaces 22 and 24 may be embedded within the walls of housing 12. The volume and dielectric properties of the other materials positioned between conductive surfaces 22 and 24 will, however, affect both the capacitance of capacitor 20 and the overall sensitivity of detector device 10. For this reason, both housing 12 and fluid conduit 14 should be substantially non-conductive so that capacitor 20 can function properly.

By way of further illustration, detector device 10 of the present invention can be conveniently used by medical personnel to detect the presence of an air bubble in the flexible tube which carries liquid from a reservoir to a patient. This tube is commonly referred to as an "IV" tube, and it is connected to a patient by means of an intravenous (IV) catheter.

For such use, housing 12 of detector device 10 may advantageously be configured such that it can be readily secured to a conventional hospital IV stand or directly attached to an IV infusion device. In either case, the IV tube 14 can be inserted into channel 13 of detector device 10 and will be releasably held within channel 13 by friction.

With tube 14 thus in place, tube 14 may be filled with the liquid to be administered to the patient. The capacitance of capacitor 20 may then be measured, and the inductance of inductor 30 is selected such that the resonant frequency of capacitor 20 and inductor 30 is substantially the same as the oscillating frequency of resonator 40.

For example, resonator 40 may have an operating frequency of 1.0 MHz. Further, the capacitance of capacitor 20 might be approximately 5.0 picofarads when tube 14 is filled with the desired liquid. Using equation (1) above, one finds that the inductance of inductor 30 must be approximately 5.1 millihenries in order for the resonant frequency of capacitor 20 and inductor 30 to be substantially the same as the oscillating frequency of resonator 40, (i.e., 1.0 MHz).

If the inductance of inductor 30 is so selected, detector device 10 will produce an output voltage 17 which oscillates at a frequency of approximately 1.0 MHz as long as tube 14 is filled with the desired liquid. At some point, however, an air bubble 15 (see FIG. 2) may enter tube 14 and flow along tube 14 until it is positioned between conductive surfaces 22 and 24 of capacitor 20. When this happens, the capacitance of capacitor 20 changes, along with the resonant frequency of capacitor 20 and inductor 30.

For example, when an air bubble is positioned in tube 14 between conductive surfaces 22 and 24 of capacitor 20, the capacitance of capacitor 20 may drop to approximately 1.25 picofarads. Using equation (1), one calculates that the resonant frequency of capacitor 20 and inductor 30 is now equal to approximately 2.0 MHz. Since this resonant frequency is now significantly different from the oscillating frequency of resonator 40 (1.0 MHz), detector device 10 will no longer produce an output voltage 17 which oscillates. Thus, by appropriately monitoring output voltage 17, the presence of an air bubble 15 between conductive surfaces 22 and 24 of capacitor 20 may be readily detected.

Advantageously, the output voltage 17 of detector device 10 may be connected to conventional electrical circuitry which will activate some type of alarm whenever output voltage 17 stops oscillating. Such circuitry is, for example, commonly used in medical devices for monitoring a patient's heart. The alarm will thus promptly notify the medical attendant that an air bubble or some other undesirable fluid is now located in tube 14 so that the patient can get the needed attention.

From the above discussion, it will be appreciated that the present invention provides a simple device which can readily distinguish between liquids and gases in a fluid column. The detector device of the present invention operates on electrical principles, and its operation is independent of the light transmission properties of the fluid in the column. Moreover, the detector device of the present invention uses readily available electrical components which can be quickly and easily assembled into a lightweight, compact unit which is very reliable. The present invention thus provides a device for distinguishing between different fluids which is inexpensive to manufacture and reliable in operation. Further, as discussed above, the detector device of the present invention can readily be used for medical applications to rapidly detect the presence of air bubbles in a column of virtually any liquid.

The invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A detector device for distinguishing between fluids having different dielectric properties, the device comprising:
   a first conductive surface;
   a second conductive surface positioned in proximity to the first conductive surface, thereby forming a capacitor in combination with the first conductive surface, the first and second conductive surfaces being further positioned so as to be capable of receiving a column of fluid therebetween;
   a voltage source;
   an inductor electrically connected between the first conductive surface and the voltage source;
   a resonator device electrically connected to the second conductive surface; and
   a transconductance amplifier means electrically connected between the resonator device and the first conductive surface.

2. A detector device as defined in claim 1 wherein the first and second conductive surfaces are substantially planar.

3. A detector device as defined in claim 1 wherein the first and second conductive surfaces are substantially parallel to one another.

4. A detector device as defined in claim 1 wherein the inductor is a variable inductance device.

5. A detector device as defined in claim 1 wherein the transconductance amplifier means comprises a field-effect transistor.

6. A detector device as defined in claim 1 wherein the resonator device has a substantially fixed oscillating frequency and wherein the resonant frequency of the capacitor and the inductor is substantially equal to the oscillating frequency of the resonator device when a column of a desired fluid is positioned between the first and second conductive surfaces of the capacitor.

7. A detector device as defined in claim 1 further comprising:
   a housing having a channel formed therein which is adapted to receive a substantially non-conductive fluid conduit; and
   wherein the first and second conductive surfaces are positioned adjacent the channel and the inductor, the resonator device, and the transconductance amplifier means are positioned within the housing.

8. A detector device as defined in claim 1 wherein the dimensions of the first and second conductive surfaces are selected such that the space between the first and second conductive surfaces is approximately just large enough to receive the smallest volume of fluid it is desired to detect.

9. A detector device for distinguishing between fluids having different dielectric properties, the device comprising:
   a first conductive surface;
   a second conductive surface positioned in proximity to the first conductive surface, thereby forming a capacitor in combination with the first conductive surface, the first and second conductive surfaces being further positioned so as to be capable of receiving a column of fluid therebetween;

a resonator device electrically connected to the second conductive surface, the resonator device having a substantially fixed oscillating frequency;

a voltage source;

an inductor electrically connected between the first conductive surface and the voltage source, the inductance of the inductor being selected such that the resonant frequency of the inductor and the capacitor is substantially equal to the oscillating frequency of the resonator device when a column of a desired fluid is positioned between the first and second conductive surfaces of the capacitor; and a transconductance amplifier means electrically connected between the resonator device and the first conductive surface.

10. A detector device as defined in claim 9 wherein the dimensions of the first and second conductive surfaces are selected such that the space between the first and second conductive surfaces is approximately just large enough to receive the smallest volume of fluid it is desired to detect.

11. A detector device as defined in claim 10 wherein the first and second conductive surfaces are substantially planar.

12. A detector device as defined in claim 11 wherein the first and second conductive surfaces are substantially parallel to one another.

13. A detector device as defined in claim 12 wherein the inductor is a variable inductance device.

14. A detector device as defined in claim 13 wherein the transconductance amplifier means comprises a field-effect transistor.

15. A detector device as defined in claim 14 further comprising:

a housing having a channel formed therein which is adapted to receive a substantially non-conductive fluid conduit; and wherein the first and second conductive surfaces are positioned adjacent the channel and the inductor, the resonator device, and the transconductance amplifier means are positioned within the housing.

16. A detector device for distinguishing between fluids having different dielectric properties, the device comprising:

a housing having a channel formed therein which is adapted to receive a substantially non-conductive fluid conduit;

a first conductive surface positioned adjacent the channel in the housing;

a second conductive surface positioned adjacent the channel in the housing, the second conductive surface forming a capacitor in combination with the first conductive surface, the first and second conductive surfaces being further positioned such that a portion of a fluid conduit which is received in the channel of the housing lies substantially between the first and second conductive surfaces;

a resonator device positioned within the housing and electrically connected to the second conductive surface, the resonator device having a substantially fixed oscillating frequency;

a voltage source;

an inductor positioned within the housing and electrically connected between the first conductive surface and the voltage source, the inductance of the inductor being selected such that the resonant frequency of the inductor and the capacitor is substantially equal to the oscillating frequency of the resonator device when the portion of a fluid conduit which lies substantially between the first and second conductive surfaces is substantially filled with a desired fluid; and a transconductance amplifier means positioned within the housing and electrically connected between the resonator device and the first conductive surface.

17. A detector device as defined in claim 16 wherein the first and second conductive surfaces are substantially planar.

18. A detector device as defined in claim 16 wherein the first and second conductive surfaces are substantially parallel to one another.

19. A detector device as defined in claim 16 wherein the inductor is a variable inductance device.

20. A detector device as defined in claim 16 wherein the transconductance amplifier means comprises a field-effect transistor.

21. A detector device as defined in claim 16 wherein the dimensions of the first and second conductive surfaces are selected such that the space between the first and second conductive surfaces is approximately just large enough to receive the smallest volume of fluid it is desired to detect.

22. A method for distinguishing between fluids having different dielectric properties, the method comprising the steps of:

forming a detector system comprising the steps of:
positioning a first conductive surface in proximity to a second conductive surface such that a column of fluid can be received therebetween and such that the first and second conductive surfaces form a capacitor;

electrically connecting the second conductive surface to a resonator device having a substantially fixed oscillating frequency;

electrically connecting an inductor between the first conductive surface and a voltage source, the inductance of the inductor being selected such that the resonant frequency of the inductor and the capacitor is substantially equal to the oscillating frequency of the resonator device when a column of a first fluid is positioned between the first and second conductive surfaces of the capacitor, the resonant frequency of the inductor and the capacitor being significantly different from the oscillating frequency of the resonator device when a column of a second fluid is positioned between the first and second conductive surfaces of the capacitor; and providing a transconductance amplifier means electrically connected between the resonator device and the first conductive surface;

detecting an oscillating output voltage from the detector system when a column of the first fluid is positioned between the first and second conductive surfaces; and detecting a substantially constant output voltage from the detector system when a column of the second fluid is positioned between the first and second conductive surfaces.

23. A method as defined in claim 22 wherein the detector system forming step further comprises the step of selecting the dimensions of the first and second conductive surfaces such that the space between the first and second conductive surfaces is approximately just large enough to receive the smallest volume of fluid it is desired to detect.

* * * * *